(12) United States Patent
Shevgoor et al.

(10) Patent No.: US 10,695,551 B2
(45) Date of Patent: Jun. 30, 2020

(54) SAFETY IV CATHETER WITH MOLDED-OPEN BLOOD CONTROL VALVE

(71) Applicant: Becton, Dickinson and Company, Franklin Lakes, NJ (US)

(72) Inventors: Siddarth Shevgoor, Laguna Beach, CA (US); Huibin Liu, West Jordan, UT (US); Ken Cluff, Saratoga Springs, UT (US); Jon Burkholz, Salt Lake City, UT (US); Ray Isaacson, Layton, UT (US); Lawrence J. Trainer, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 171 days.

(21) Appl. No.: 15/760,816

(22) PCT Filed: Sep. 16, 2016

(86) PCT No.: PCT/US2016/052232
§ 371 (c)(1),
(2) Date: Mar. 16, 2018

(87) PCT Pub. No.: WO2017/049150
PCT Pub. Date: Mar. 23, 2017

(65) Prior Publication Data
US 2018/0256885 A1 Sep. 13, 2018

Related U.S. Application Data

(60) Provisional application No. 62/220,653, filed on Sep. 18, 2015.

(51) Int. Cl.
*A61M 39/26* (2006.01)
*A61M 25/06* (2006.01)
(Continued)

(52) U.S. Cl.
CPC ............ *A61M 39/26* (2013.01); *A61M 25/06* (2013.01); *A61M 25/0606* (2013.01);
(Continued)

(58) Field of Classification Search
CPC .... A61M 2039/062; A61M 2039/2493; A61M 2039/266; A61M 25/00; A61M 25/0009;
(Continued)

(56) References Cited

U.S. PATENT DOCUMENTS 5,549,651 A  8/1996 Lynn
5,967,490 A  10/1999 Pike
(Continued)

FOREIGN PATENT DOCUMENTS

CN       203724591 U    7/2014
WO    WO-2004000408 A1  12/2003
WO    WO-2014/150530 A1  9/2014

*Primary Examiner* — Jason E Flick
(74) *Attorney, Agent, or Firm* — Dickinson Wright PLLC

(57) ABSTRACT

A catheter assembly (10) comprising a catheter (18), a needle (12) having a sharp distal tip (13), and a catheter hub (14) connected to the catheter (18) having the needle (12) passing therethrough, the catheter hub (14) including a valve (19) having a preformed opening (22) that selectively permits or blocks a flow of fluid through the catheter (18), a first inner diameter (32) that closes the valve (19), and a second inner diameter (30) larger than the first inner diameter (32), the second inner diameter (30) opening the valve (19), wherein the valve (19) is in an open position upon axially compressing the valve (19) into engagement with the second inner diameter (30) of the catheter hub (14), and the valve (19) is in a closed position upon releasing the valve (19) to engage the first inner diameter (32) of the catheter hub (14).

17 Claims, 14 Drawing Sheets

(51) Int. Cl.
*A61M 39/06* (2006.01)
*A61M 5/32* (2006.01)
*A61M 39/24* (2006.01)

(52) U.S. Cl.
CPC ....... *A61M 39/0606* (2013.01); *A61M 5/3273* (2013.01); *A61M 2039/062* (2013.01); *A61M 2039/064* (2013.01); *A61M 2039/2433* (2013.01)

(58) Field of Classification Search
CPC .......... A61M 25/0097; A61M 25/0606; A61M 39/00; A61M 39/02; A61M 39/06; A61M 39/0693; A61M 39/10; A61M 39/22; A61M 39/24; A61M 39/26; A61M 2039/064; A61M 2039/2433; A61M 25/06; A61M 39/0606; A61M 2039/0633; A61M 5/3273
See application file for complete search history.

(56) References Cited

U.S. PATENT DOCUMENTS

| | | | |
|---|---|---|---|
| 6,663,592 B2 | 12/2003 | Rhad et al. | |
| 8,979,802 B2 | 3/2015 | Woehr | |
| 2002/0128604 A1* | 9/2002 | Nakajima | A61M 39/0693 604/164.01 |
| 2004/0127854 A1 | 7/2004 | Leinsing et al. | |
| 2006/0276751 A1* | 12/2006 | Haberland | A61B 17/3462 604/167.01 |
| 2006/0293560 A1* | 12/2006 | Nguyen | A61B 17/42 600/104 |
| 2009/0005741 A1 | 1/2009 | Martin et al. | |
| 2014/0018738 A1 | 1/2014 | Steube et al. | |
| 2014/0276434 A1* | 9/2014 | Woehr | A61M 25/0075 604/164.08 |
| 2015/0202421 A1 | 7/2015 | Ma et al. | |
| 2016/0001056 A1* | 1/2016 | Nelson | A61M 39/045 604/247 |

* cited by examiner

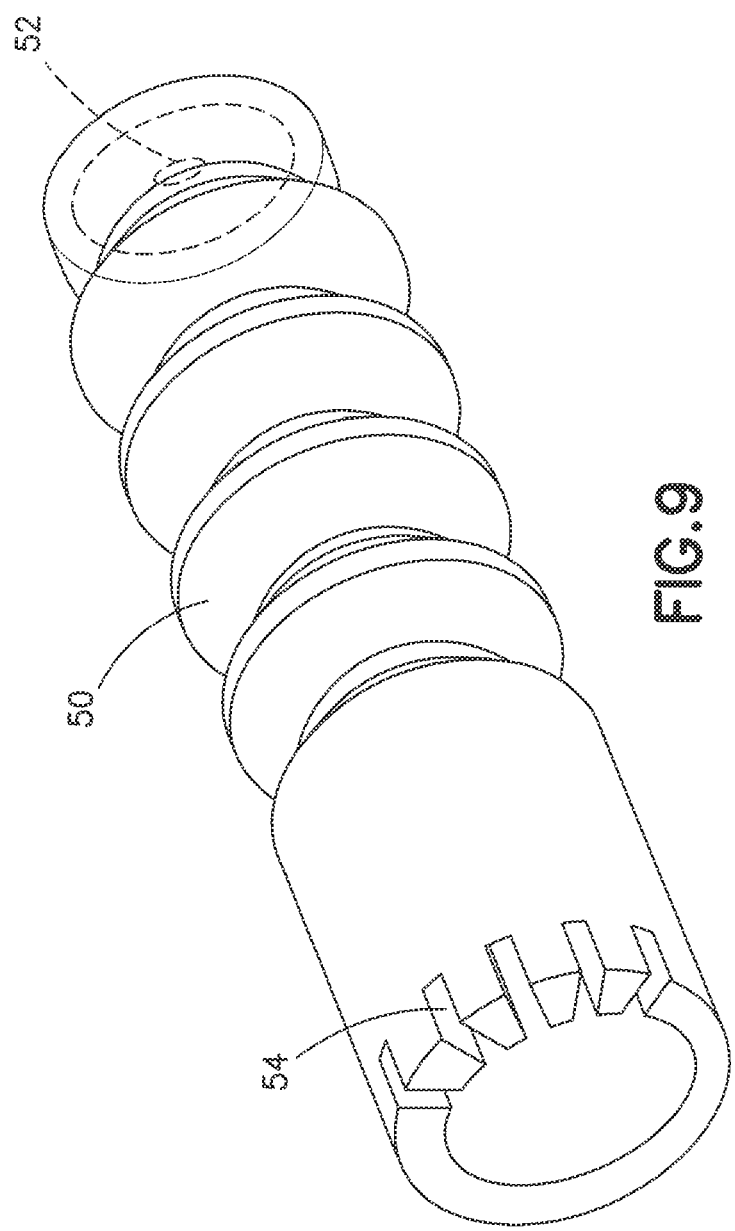

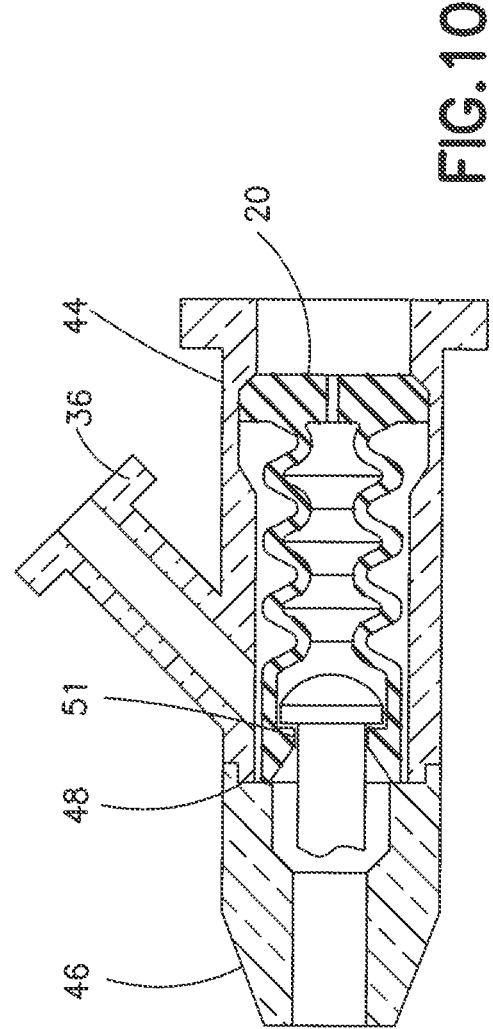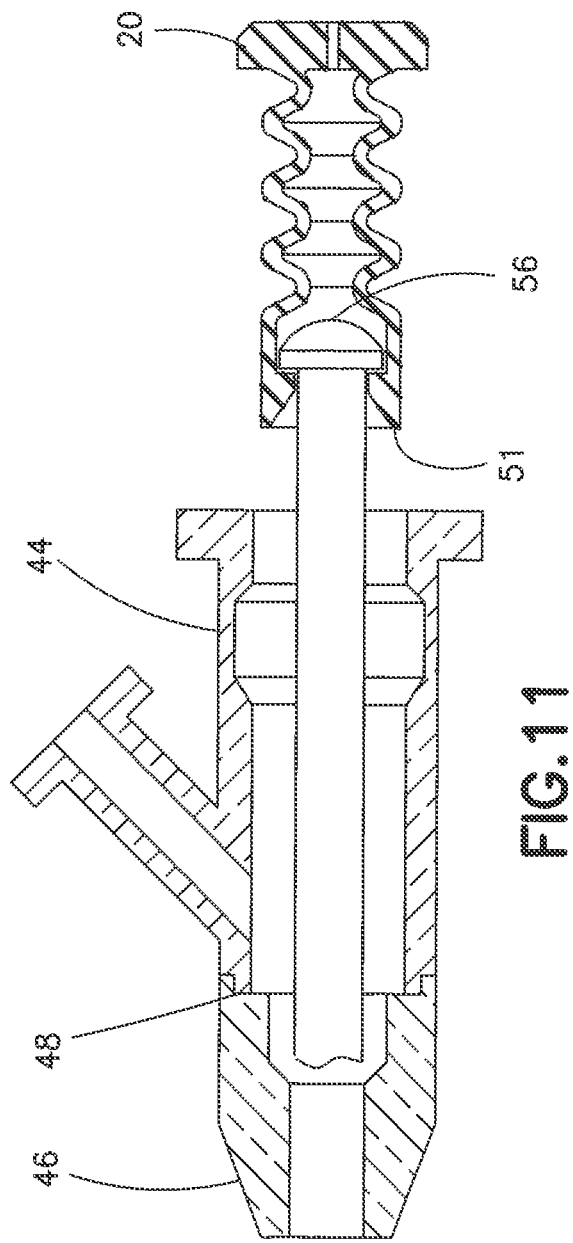

SAFETY IV CATHETER WITH MOLDED-OPEN BLOOD CONTROL VALVE

This application claims the benefit under 35 U.S.C. § 119(e) of U.S. Provisional Patent Application Ser. No. 62/220,653, filed on Sep. 18, 2015, the entire content, disclosure and subject matter of such application being expressly incorporated herein by reference.

FIELD

Various exemplary embodiments of the invention relate to catheter assemblies.

BACKGROUND

Catheter assemblies are used to place a catheter into the vascular system of a patient. Once in place, catheters such as intravenous catheters may be used to infuse fluids including normal saline, medicinal compounds, and/or nutritional compositions into a patient in need of such treatment. Catheters additionally enable the removal of fluids from the circulatory system and monitoring of conditions within the vascular system of the patient.

SUMMARY OF THE INVENTION

It is an aspect of the present invention to provide a catheter assembly including a molded-open blood control valve. Generally, septums in the prior art are closed in their natural state and need to be pierced or otherwise engaged to be opened. On the other hand, the septum disclosed herein is open in its natural state and is closed by its housing or an external force, for example. Such a septum provides a plurality of advantages disclosed herein.

Additionally, the catheter assembly includes a ported catheter where the catheter hub has a side port. The septum disclosed herein is advantageously able to regulate fluid flow from the catheter and the side port simultaneously and independently. Finally, the catheter assembly disclosed herein includes a needle having a reduced diameter that engages the septum during storage to advantageously minimize compression setting.

The embodiments of the catheter assembly disclosed herein provide advantages of fewer components, improved manufacturing and assembly and more efficient and more reliable operation.

The foregoing and/or other aspects of the present invention can be achieved by providing a catheter assembly comprising a catheter, a needle having a sharp distal tip disposed within the catheter, and a catheter hub connected to the catheter having the needle passing therethrough, the catheter hub including a valve having a preformed opening that selectively permits or blocks a flow of fluid through the catheter, a first inner diameter that closes the valve, and a second inner diameter larger than the first inner diameter, the second inner diameter opening the valve, wherein the valve is in an open position upon compressing the valve into engagement with the second inner diameter of the catheter hub, and the valve is in a closed position upon releasing the valve to engage the first inner diameter of the catheter hub.

The foregoing and/or other aspects of the present invention can further be achieved by providing a catheter assembly comprising a catheter, a needle having a sharp distal tip disposed within the catheter, a catheter hub connected to the catheter having the needle passing therethrough, the catheter hub including a valve having a preformed opening that selectively permits or blocks a flow of fluid through the catheter, a first inner diameter that closes the valve, and a second inner diameter larger than the first inner diameter, the second inner diameter opening the valve, and a needle shield that houses the needle, wherein the valve is in an open position upon engaging the needle shield to the catheter hub and compressing the valve into the second inner diameter of the catheter hub, and the valve is in a closed position upon disengaging the needle shield from the catheter assembly, thus releasing the valve to engage the first inner diameter of the catheter hub.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which:

FIG. 9 illustrates a side perspective view of an exemplary embodiment of the septum including axial flow channels;

FIG. 10 illustrates a cross sectional view of an exemplary embodiment of the catheter hub assembly including a side port and a septum;

FIG. 11 illustrates a cross sectional view of an exemplary embodiment of the catheter hub assembly including a side port and tooling equipment used to assemble the septum;

DETAILED DESCRIPTION OF EXEMPLARY EMBODIMENTS

Figure 1:
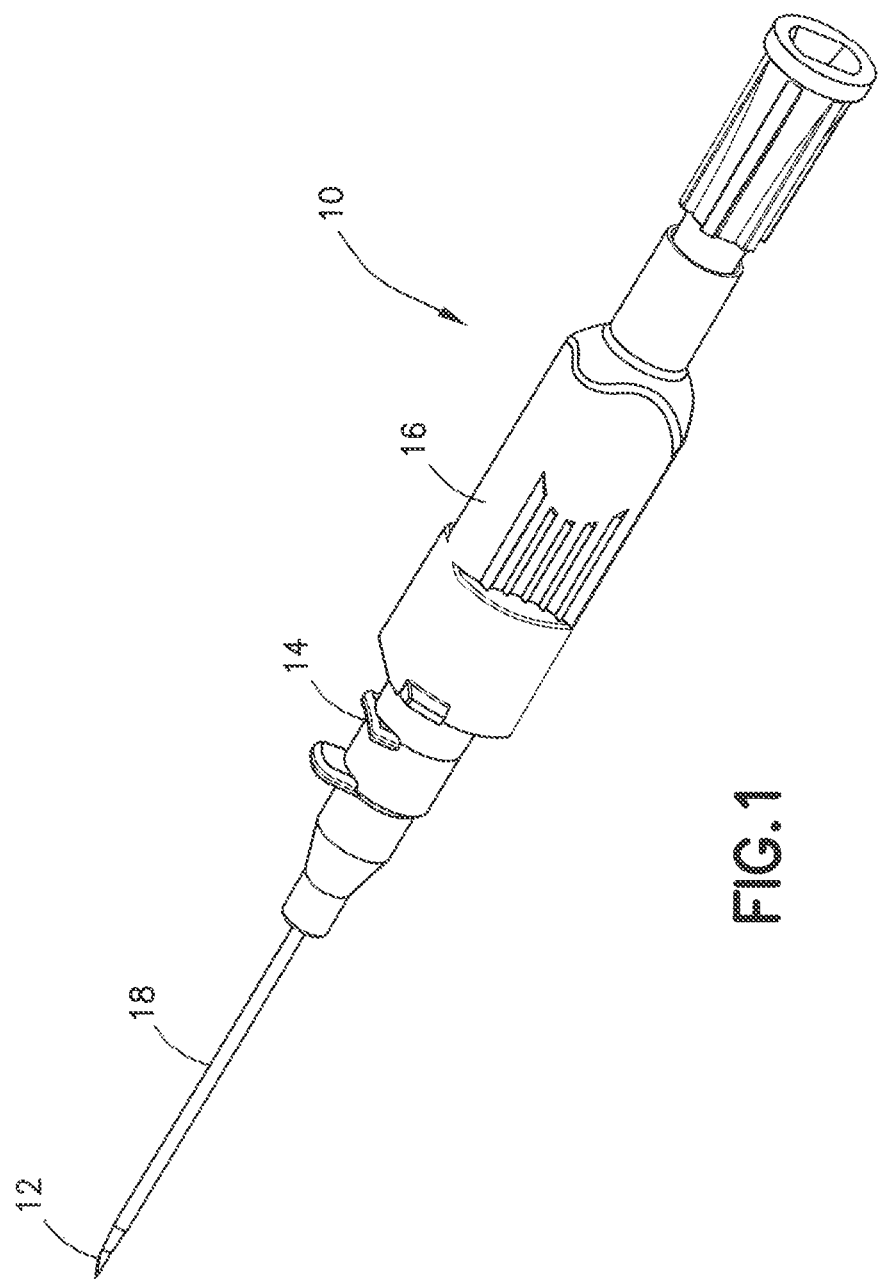
FIG. 1 illustrates a perspective view of an exemplary catheter assembly.

A catheter assembly 10, as shown in FIG. 1, includes a hollow introducer needle 12, a catheter hub 14, and a needle hub 16. The introducer needle 12 has a sharpened distal tip 13 and extends through the catheter hub 14. A flexible catheter tube 18 extends from the distal end of the catheter hub 14, with the needle 12 passing through the catheter tube 18. The flexible catheter tube 18 extends through the catheter opening. Initially, the needle 12 is inserted into a patient's vein. The catheter tube 18 is pushed along the needle 12 and into the vein following the needle 12. After the catheter tube 18 is inserted, the needle 12 is removed from the patient's vein and the catheter hub 14, leaving the catheter tube 18 in the patient as the needle 12 is discarded.

Figure 2:
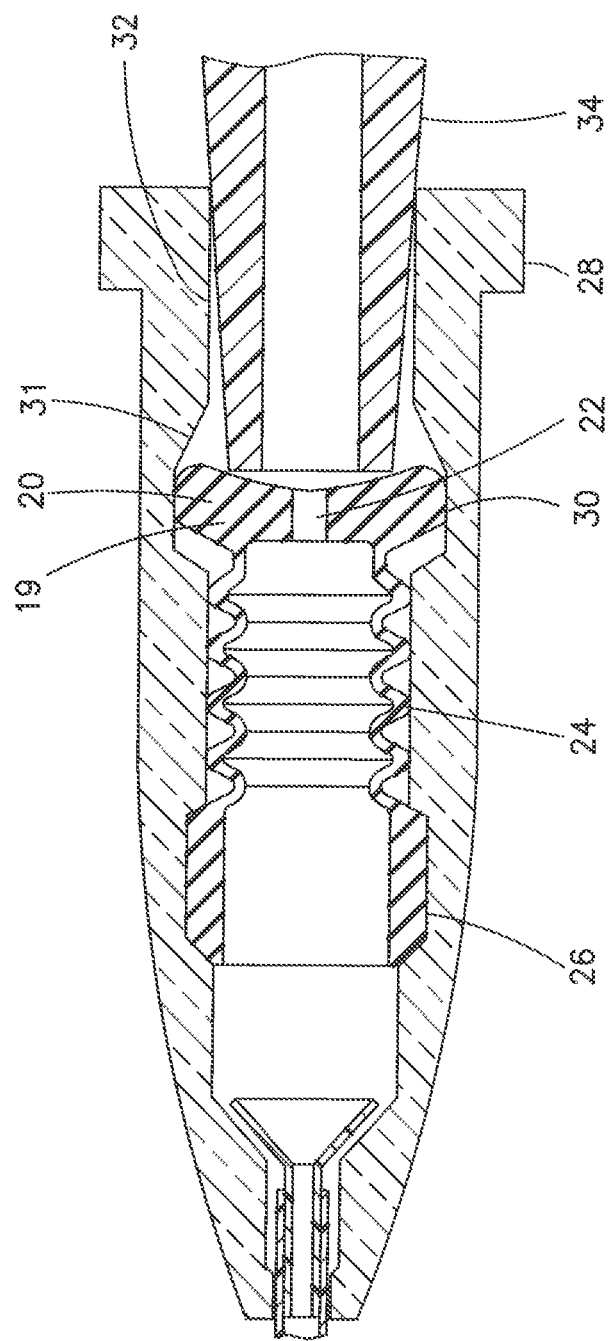
FIG. 2 illustrates a cross sectional view of a luer engaging a catheter hub of the catheter assembly of FIG. 1.

FIG. 2 illustrates a cross-sectional view of an exemplary catheter hub assembly. The catheter hub assembly preferably includes a blood control valve 19 that includes a septum 20 and a compressible section such as a bellows 24, for example. The septum 20 is positioned in the catheter hub 28 and functions as a valve that forms a fluid-tight seal and selectively admits fluid to or from the flexible catheter tube 18. In other words, the valve selectively permits or blocks the flow of fluid through the flexible catheter tube 18.

The septum 20 may be used in any of the embodiments discussed herein. Other septum configurations may be used as would be understood by one of ordinary skill in the art. When the catheter tube 18 is initially inserted into a patient, and the introducer needle 12 is removed, the septum 20 prevents blood from flowing through the channel and out of the distal end. The septum 20 is made of an elastic material to form the valve, for example silicone rubber. Other elastic materials may be used and non-elastic materials may be incorporated in the septum 20 as needed.

The septum 20 comprises a preformed opening 22 or a molded-open slit. The preformed opening 22 of the septum 20 is preferably formed when the septum 20 is originally manufactured or in a subsequent machining or cutting operation. Accordingly, when the septum 20 is in its natural, uncompressed, free or relaxed state, the preformed opening 22 is open, thus placing the septum 20 in an open position and acting as an open fluid channel.

On the other hand, when the septum 20 is radially compressed around the preformed opening 22, the preformed opening 22 closes and seals to place the septum 20 in a closed position. Generally, septums in the prior art are closed in their natural state and need to be pierced, deformed or otherwise engaged to be opened. By contrast, the septum 20 according to this embodiment is open in its natural state and is engaged to be closed.

The septum 20 includes a bellows 24 that acts as a spring member. The axial spring of the bellows 24 can be simply a tube or can preferably include molded undulations or any other shape that allow the bellows 24 to resiliently compress in a predictable manner and still provide enough spring force for the septum 20 to operate. The bellows 24 is expanded in its natural state and compressed during operation to allow the septum 20 to move between the open and closed positions.

The bellows 24 is preferably made of an elastic material, for example silicone rubber. Other elastic materials may be used and non-elastic materials may be incorporated in the bellows 24 as needed. According to one embodiment, the bellows 24 can be replaced or augmented by a spring member such as a coil spring and used in a catheter hub assembly to cooperate with the preformed opening 22 of the septum 20.

The septum 20 further includes a mounting surface 26. The mounting surface 26 secures the septum 20 at a position within the catheter hub assembly. Specifically, the mounting surface 26 is more rigid compared to the rest of the septum 20. The mounting surface 26 also expands in the inner diameter of the catheter hub 28. Such expansion provides a clamping force to secure the septum 20 and increased friction to prevent the septum 20 from being displaced. The bellows 24 is disposed between the mounting surface 26 and the preformed opening 22. Thus, after securing the mounting surface 26 of the septum 20, the septum 20 can operate between the relaxed and compressed positions.

As illustrated in FIG. 2, a distal end of the catheter hub 28 includes a catheter opening and a proximal end includes a Luer connector opening. The inner surface at the proximal end of the catheter hub 28 surrounds a channel that permits fluid passage through the catheter hub 28. The outer surface of the catheter hub 28 includes one or more projections to secure a Luer connector 34 to the catheter hub 28. The projections may form a threaded connection with the Luer connector 34 or they may connect to the Luer connector 34 through a snap fit or other twisting connection.

One example of a standard connection is a LUER-LOK® connection. Certain types of Luer connectors 34 utilize a slip fit into the catheter hub 28. Preferably, the Luer connector 34 travels a significant distance into the catheter hub 28 prior to contacting the septum 20. The extended inner diameter at the proximal end of the catheter hub 28 advantageously allows the Luer connector 34 to be centered in the catheter assembly. The catheter hub 28 may be made from a polymer material that is transparent or semi-transparent so that fluid flow through the catheter hub may be observed by a user or it may be made from an opaque material.

The catheter hub 28 includes various inner diameters that interact with the septum 20 to provide effective operation. The catheter hub 28 includes a free diameter 30 and a compression diameter 32. The free diameter 30 is larger than the compression diameter 32. The free diameter 30 is preferably connected to the compression diameter 32 by a chamfered surface 31. When a surface surrounding the preformed opening 22 of the septum 20 is disposed in the free diameter 30, the septum 20 is in an open position where fluid is capable of flowing through the preformed opening 22. On the other hand, when the surface surrounding the preformed opening 22 of the septum 20 is disposed in the compression diameter 32 and/or in the chamfered surface 31, the septum 20 is radially compressed causing the preformed opening 22 to close and seal. This places the septum 20 in a closed position where fluid is not able to flow through the preformed opening 22.

The septum 20 is moved from the closed position to the open position by the Luer connector 34, for example. In operation, the Luer connector 34 is supported and centered by the inner diameter at the distal end of the catheter hub prior to interacting with the septum 20. When the Luer connector 34 initially contacts the septum 20, the surface surrounding the preformed opening 22 of the septum 20 is disposed in the compression diameter 32 and/or the chamfered surface 31 of the catheter hub 28. In this position, the septum 20 is in the closed position where the preformed opening 22 is closed and sealed.

To open the septum 20 (open position), a user can push the Luer connector 34 into the catheter hub 28, which pushes the surface surrounding the preformed opening 22 of the septum 20 into a free diameter 30 of the catheter hub 28 while axially compressing the bellows 24. In this position, the septum 20 expands radially, causing the preformed opening 22 to open and allowing a path for fluid to flow. At the same time, the septum 20 is compressed axially at the bellows 24 to create an increased reacting axial force.

Subsequently, when the user removes the Luer connector 34 from the catheter hub 28, the bellows 24 of the septum 20 expands and causes the surface surrounding the preformed opening 22 of the septum 20 to enter into the chamfered surface 31 and/or the compression diameter 32 of the catheter hub 28 and enter into the closed position. In the closed position of the catheter hub 28, the bellows 24 preferably continues to be partially axially compressed to create a force so that the septum 20 establishes a sealing surface with the free diameter 30, the chamfered surface 31 and the compression diameter 32.

In addition, the septum 20 does not only operate between a fully relaxed position and a fully compressed position. The septum 20 can also operate between a less compressed position and more compressed position. The septum 20 can be open when less (partially) compressed and closed when more compressed. Similarly, the septum 20 can operate in a less relaxed position and a more relaxed position. The septum 20 can be open when more relaxed and closed when less (partially) relaxed. Such versatility can be useful in a variety of pressure gradients experienced by the septum 20. The features of the exemplary septum depicted in FIG. 2 may be combined with features of the other exemplary embodiments disclosed herein.

Figure 3:
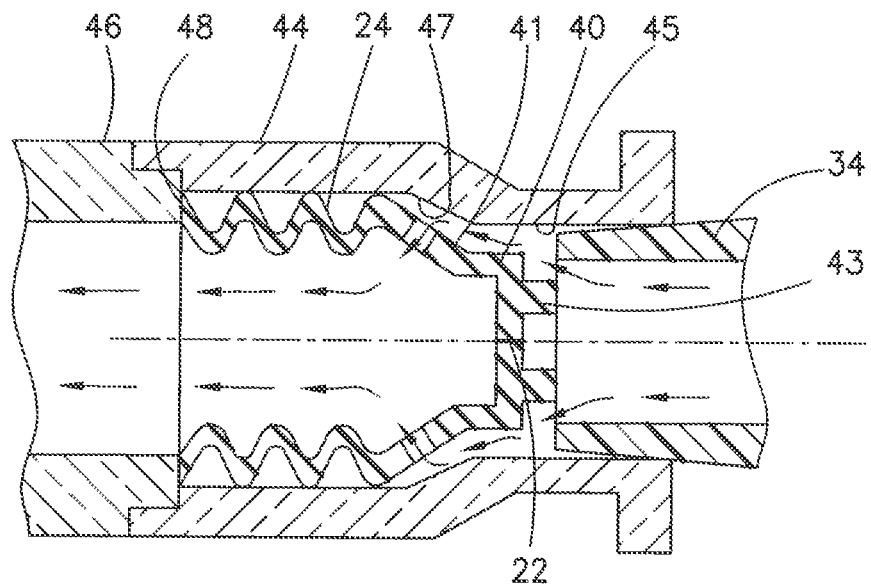
FIG. 3 illustrates a cross sectional view of another exemplary embodiment of a catheter hub assembly in an open position.
Figure 4:
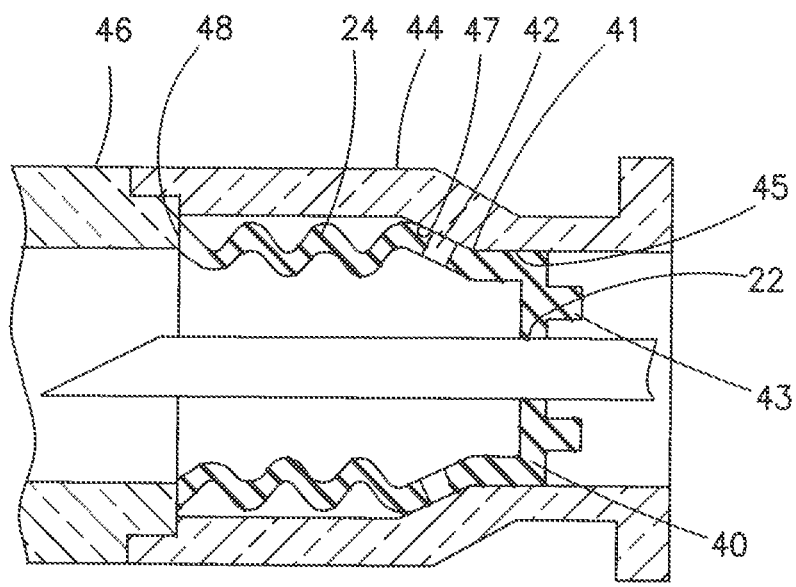
FIG. 4 illustrates another cross sectional view of the catheter hub assembly of FIG. 3 in a closed position.

FIGS. 3 and 4 illustrate a septum 40 in a catheter hub assembly according to another exemplary embodiment. FIG. 3 depicts the septum 40 in an open position and FIG. 4 depicts the septum 40 in a closed position. Specifically, the catheter hub assembly includes a two-piece catheter hub including a first catheter hub portion 44 and a second catheter hub portion 46. A two-piece construction advantageously provides improved assembly and reduced manufacturing cost. The second catheter hub portion 46 also includes an undercut surface 48 that acts as a stopping surface for assembly and operation of the septum 40.

The septum 40 includes a sealing surface 41 that interfaces with an inner diameter 45 and a chamfered surface 47 of the first catheter hub portion 44. The sealing surface 41 is disposed between the bellows 24 and the preformed opening 22. The sealing surface 41 of the septum 40 includes a plurality of through holes 42 spaced along its perimeter. A variety of shapes, sizes and spacing of the plurality of through holes 42 is contemplated. On a proximal end of the septum 40 includes a boss 43 that mates with a Luer connector 34, for example. The boss 43 and Luer connector 34 interface aids in operation of the septum 40. The septum 40 also includes bellows 24 for proper operation of the septum 40 as further described below.

When the catheter hub assembly is in the closed state, as illustrated in FIG. 4, the bellows 24 of the septum 40 creates a force from the undercut surface 48 of the second catheter hub portion 46 and travels through the septum 40 to the chamfered surface 47 and the inner diameter 45 of the first catheter hub portion 44. This force causes the sealing surface 41 of the septum 40 engage the inner diameter 45 and the chamfered surface 47 of the first catheter hub portion 44. As a result, no fluid can pass through the septum 40.

The boss 43 of the septum 40 centers the Luer connector 34 upon engagement. When the Luer connector 34 engages the boss 43 of the septum 40 and applies axial pressure sufficient to overcome the pressure exerted by the bellows 24, the septum 40 moves away from the inner diameter 45 and the chamfered surface 47 of the first catheter hub portion 44. Thus, the septum 40 enters into an open position as illustrated in FIG. 3. When the septum 40 opens, the fluid travels between the sealing surface 41 and the first catheter hub portion 44. Next, the fluid travels through the plurality of through holes 42 and enters into the catheter hub assembly. Upon release of the axial pressure from the Luer connector 34, the pressure in the bellows 24 forces the septum 40 to return to the closed position as illustrated in FIG. 4 and prevents fluid from entering the catheter hub assembly. The features of the exemplary septum depicted in FIGS. 3 and 4 may be combined with features of the other exemplary embodiments disclosed herein.

Figure 5:
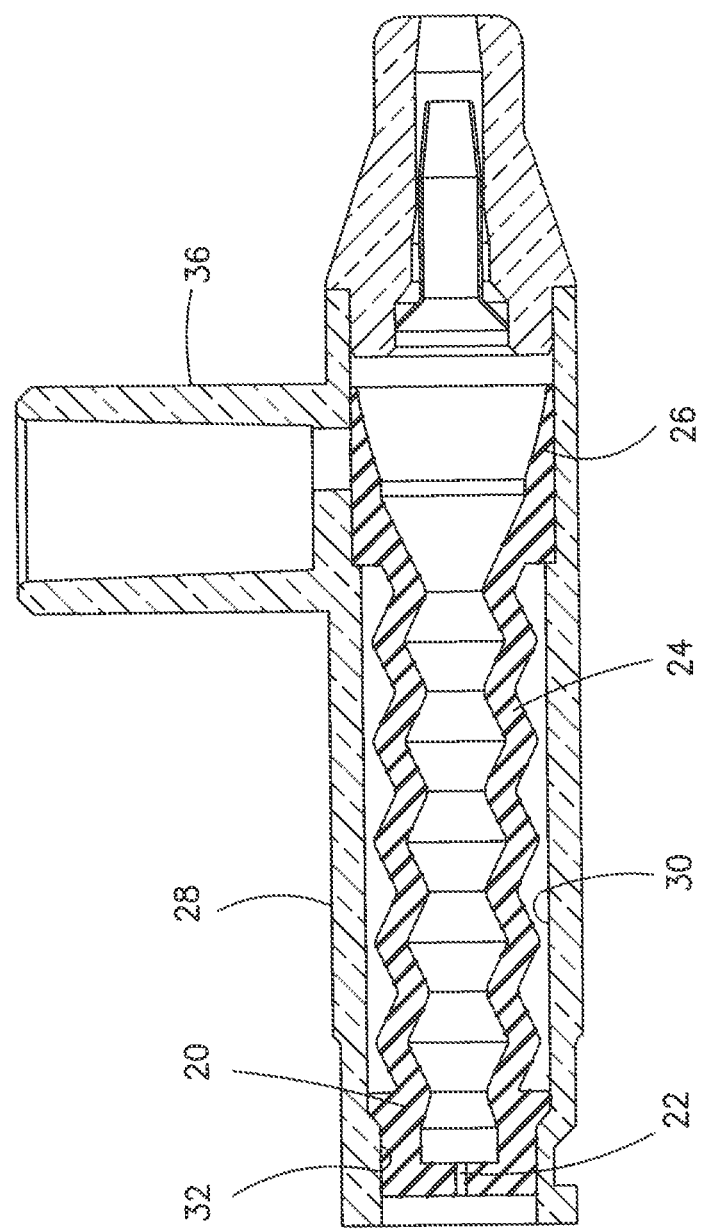
FIG. 5 illustrates a cross sectional view of the catheter assembly where the septum is in a closed position.
Figure 6:
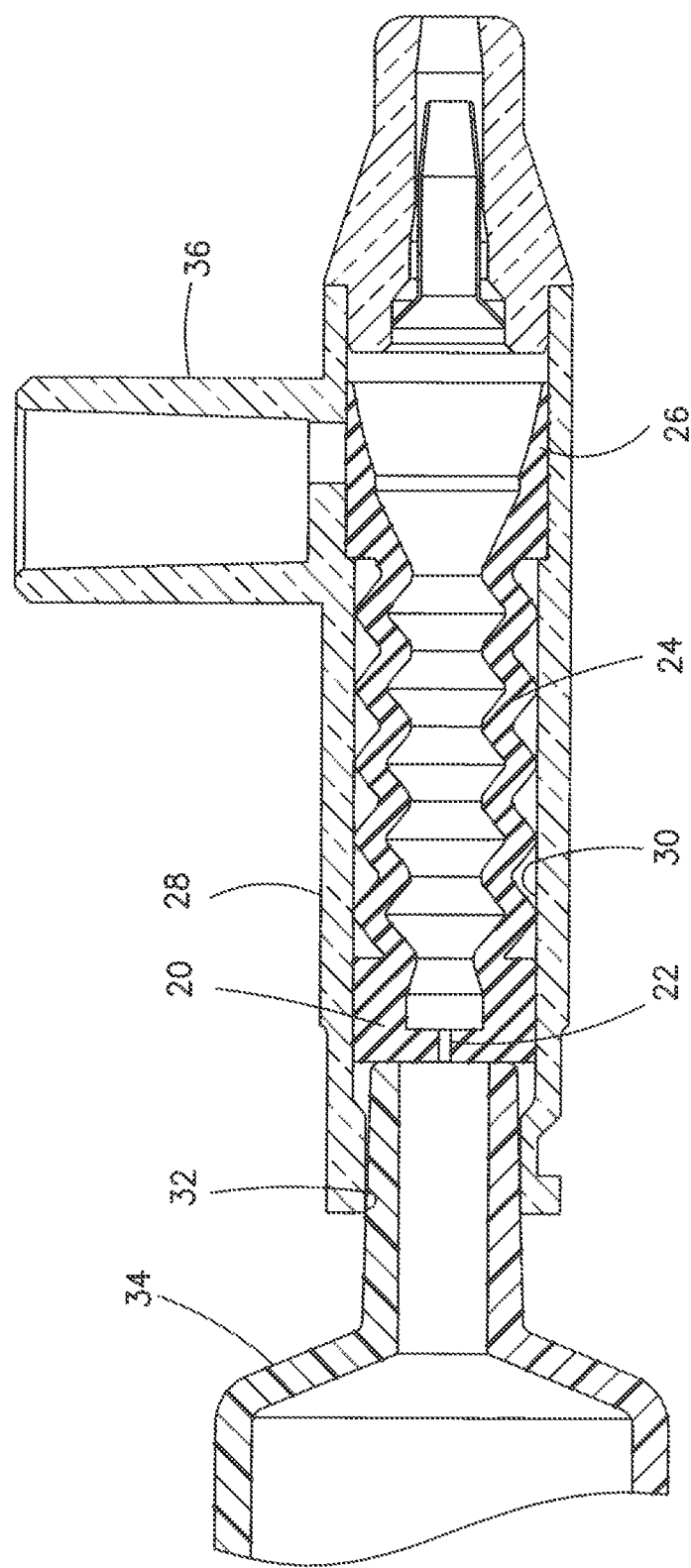
FIG. 6 illustrates another cross sectional view of the catheter assembly of FIG. 5 where the septum is in an open position.
Figure 7:
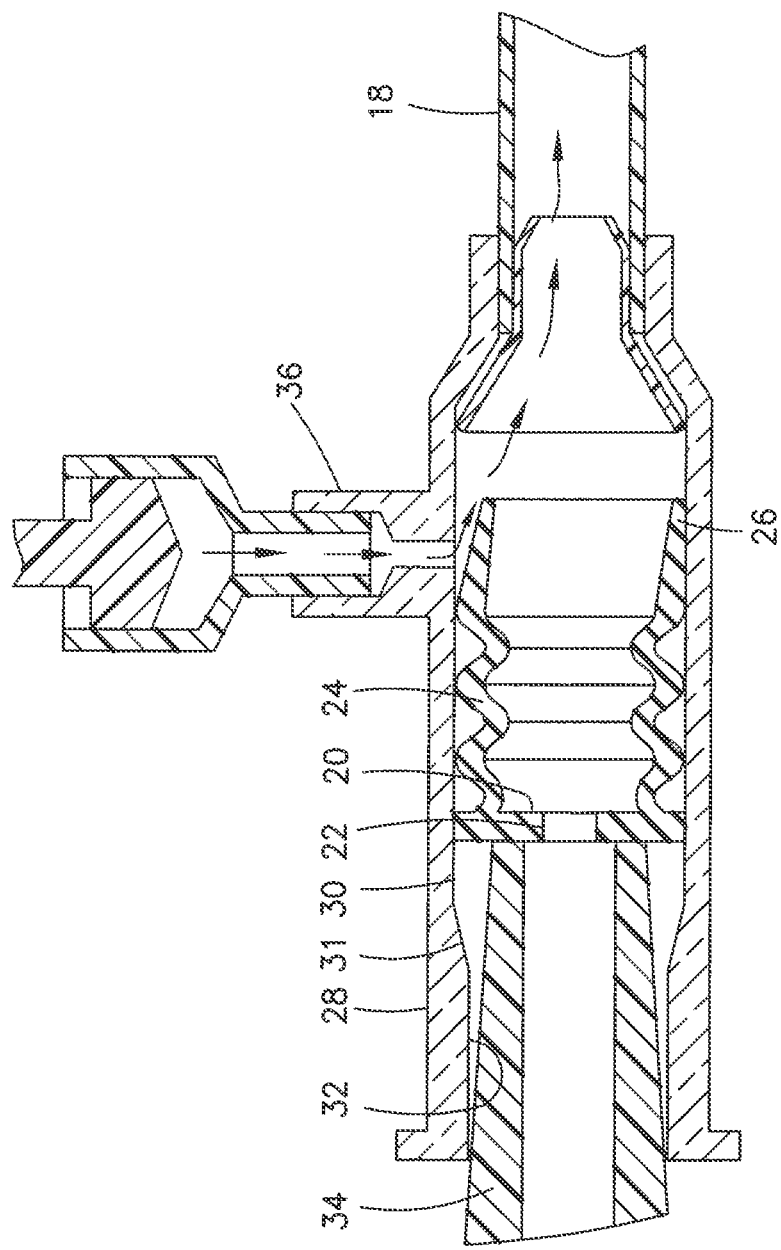
FIG. 7 illustrates another cross sectional view of the catheter assembly of FIG. 5 where the septum is in an open position at a luer connector and at a side port.

FIGS. 5-7 illustrate a preferred embodiment of the catheter hub assembly of FIG. 2 and further include a side port 36. The catheter hub assembly of this embodiment operates in a similar manner as described in FIG. 2. However, the mounting surface 26 of the septum 20 also selectively permits or blocks a flow of fluid entering through the side port 36. The selective opening and closing of the septum 20 at the preformed opening 22 and at the mounting surface 26 operate independently from each other.

The mounting surface 26 seals the side port 36 via its rigidity and its applied sealing force due to the radial expansion as described in the embodiments above. As illustrated in FIG. 7, to allow for the selective opening of the septum 20 at the mounting surface 26, the mounting surface 26 has a variable thickness across the length of its surface. Preferably, the mounting surface 26 decreases in thickness while approaching the distal end of the septum 20. In this manner, the flexibility and stiffness of the mounting surface 26 is adjusted for effective operation as described below.

In operation, when the fluid force from the side port 36 overcomes the counteracting forces of the mounting surface 26 (through the material stiffness), the septum 20 at the mounting surface 26 will flex and open (see FIG. 7) to allow fluid to enter the catheter hub 28 (open position). When the fluid force from the side port 36 is less than the counteracting forces of the mounting surface 26 (through the material stiffness), the septum 20 at the mounting surface 26 will close (see FIGS. 5 and 6) and return to its initial state (closed position). Thus, the septum 20 is advantageously able to regulate fluid flow from the catheter and the side port simultaneously, yet independently.

The septum 20 can allow fluid to enter the catheter hub 28 via the Luer connector 34 and the side port 36 in a variety of different operational modes. For example, as illustrated in FIG. 6, the preformed opening 22 can be in the open position while the mounting surface 26 can be in the closed position. In another operational mode, as illustrated in FIG. 7, the preformed opening 22 and the mounting surface 26 can both be in the open position. Additionally, the preformed opening 22 can be in the closed position while the mounting surface 26 can be in the open position. Finally, as illustrated in FIG. 5, the preformed opening 22 and the mounting surface 26 can both be in the closed position. The features of the exemplary septum depicted in FIGS. 5-7 may be combined with features of the other exemplary embodiments disclosed herein.

Figure 8:
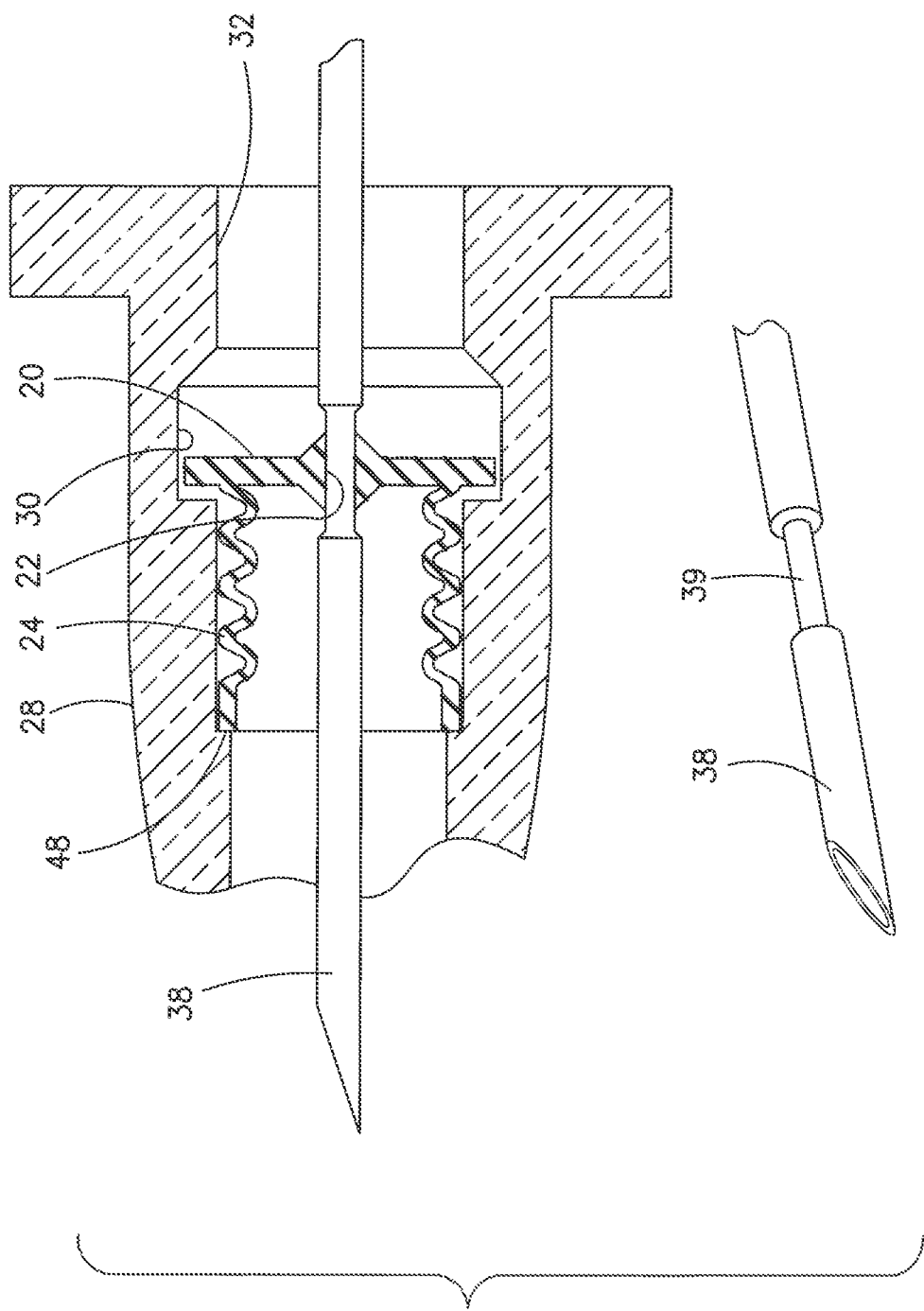
FIG. 8 illustrates a cross sectional view of another exemplary embodiment of a catheter hub assembly with a needle including a reduced diameter section.

FIG. 8 illustrates an exemplary embodiment of a catheter hub assembly with a needle 38 having a reduced diameter 39. During storage of the catheter assembly, it may not be desirable to dispose the septum 20 in the closed position because the elasticity of the septum 20 may be compromised over the extended period of time. In other words, if the septum 20 is disposed in the compression diameter 32 of the catheter hub 28 for an extended period of time, the septum 20 may enter into a compression set and begin to lose the ability to effectively transition between the opened and closed positions. If the septum 20 enters into a compression set, tire sealing strength over the life of the septum 20 will be compromised.

To address the potential problem described above, according to one embodiment the septum 20 is disposed in the free diameter 30 of the catheter hub 28 and placed in the open position. Meanwhile, the needle 38 is disposed inside the catheter assembly and the reduced diameter 39 of the needle 38 is positioned at the free diameter 30 of the catheter hub 28 where the preformed opening 22 of the septum 20 is located. This open position is maintained during storage. Thus, the catheter assembly can be in storage for long periods of time while applying minimal stress to the preformed opening 22 of the septum 20.

When the catheter assembly is ready for use, the needle 38 can aid in the placement of the flexible catheter tube 18 into the patient. Subsequently, the needle 38 is removed and the catheter assembly can operate in a similar manner described in the above embodiments. Accordingly, the reduced diameter 39 in the needle 38 will not have an effect on the flow of fluid or general operation of the catheter assembly. The features of the exemplary needle depicted in FIG. 8 may be combined with features of the other exemplary embodiments disclosed herein.

As illustrated in FIG. 9, a plurality of axial flow channels 54 can be disposed on a distal end of the septum 50 while the preformed opening 52 is disposed on the proximal end of the septum 50. The flow channels 54 are disposed on an outer circumference of the septum 50. Five flow channels 54 are illustrated, although various quantities and positions are contemplated. The flow channels 54 have an appropriate width and depth so that when the septum 50 is not opened, blood can enter into the septum 50 and air can escape the space distal of the septum 50 in the front portion of the catheter hub 28. At the same time, the flow channels 54 are sized small enough to prevent the blood from exiting past the septum 50 (at least for some period of time). Such a configuration is possible because the intermolecular forces in the blood are greater than the intermolecular forces in air. The features of the exemplary septum depicted in FIG. 9 may be combined with features of the other exemplary embodiments disclosed herein.

FIGS. 10 and 11 illustrate a cross sectional view of a two-piece catheter hub assembly with a side port 36. The catheter hub assembly includes a first catheter hub portion 44 and a second catheter hub portion 46. The first catheter hub portion 44 includes the side port 36. A centerline of the side port 36 is preferably positioned at an angle less than 90 degrees with respect to a centerline of the catheter hub assembly. More preferably, the centerline of the side port 36 is angled at 45 degrees with respect to the centerline of the catheter hub assembly.

The side port 36 is disposed near the distal end of the first catheter hub portion 44. The second catheter hub portion 46 includes an undercut surface 48 that contacts with the distal end of the first catheter hub portion 44. When the first and second catheter hub portions 44, 46 are assembled, they are secured together preferably by a weld joint, but can alternately be secured by a press fit, a snap fit or an adhesive joint. Angling the side port 36 as described above provides enough clearance for the welding process to take place.

After the catheter hub assembly is welded together, tooling equipment 56 is used to aid in assembling the septum 20 to the catheter hub assembly. Specifically, as illustrated in FIG. 11, the tooling equipment 56 is secured to the septum 20 via a notch 51 at the distal end of the septum 20. The tooling equipment 56 subsequently pulls the septum 20 into the catheter hub assembly until the septum 20 contacts the undercut surface 48 of the second catheter hub portion 46, as illustrated in FIG. 10. Afterward, the tooling equipment 56 is removed and the catheter hub assembly operates in a similar manner as described in the embodiments above. Accordingly, the septum 20 is capable of sealing the catheter hub assembly at the proximal end and at the side port 36. The features of the exemplary catheter hub assembly method depicted in FIGS. 10 and 11 may be combined with features of the other exemplary embodiments disclosed herein.

Figure 12:
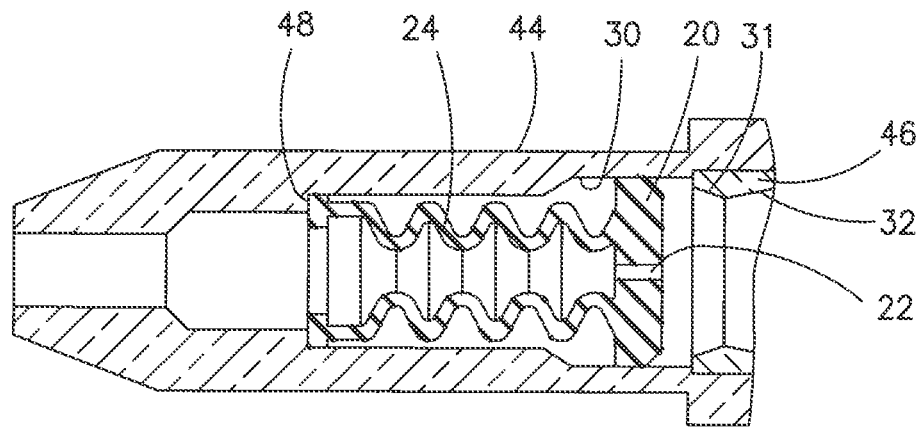
FIG. 12 illustrates a cross sectional view of an exemplary embodiment of a two-piece catheter assembly.

FIG. 12 illustrates an alternate embodiment of a two-piece catheter hub assembly. The two piece catheter hub assembly includes a first catheter hub portion 44 and a second catheter hub portion 46. The first catheter hub portion 44 includes a free diameter 30 and an undercut surface 48 while the second catheter hub portion 46 includes a compression diameter 32 and a chamfered surface 31.

After the valve 19 is assembled into the first catheter hub portion 44 and contacts the undercut surface 48, the second catheter hub portion 46 is fixedly mounted to the inner diameter of the first catheter hub portion 44 via a press fit, for example. Accordingly, the septum 20 having a preformed opening 22 and bellows 24 are able to move from the free diameter 30 of the first catheter hub portion 44 to the chamfered surface 31 and the compression diameter 32 of the second catheter hub portion 46 to achieve the open and closed positions in a similar manner as described in the embodiments above. The features of the exemplary catheter hub assembly depicted in FIG. 12 may be combined with features of the other exemplary embodiments disclosed herein.

Figure 13:
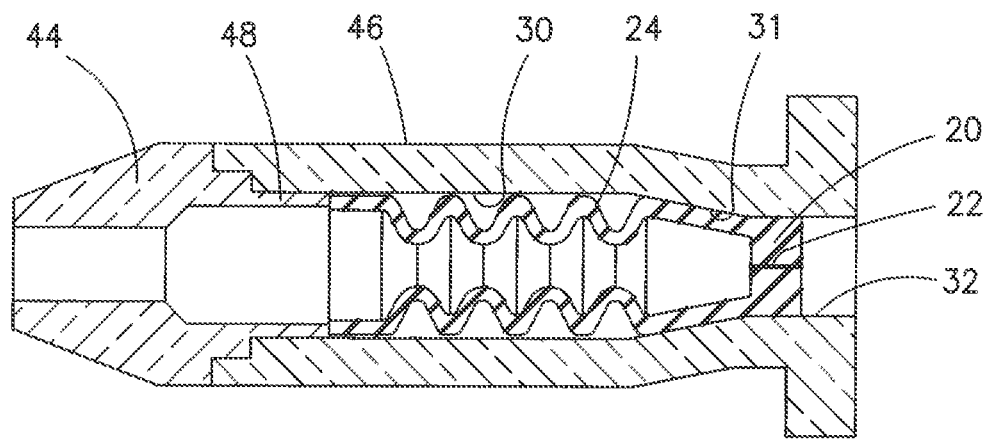
FIG. 13 illustrates a cross sectional view of another exemplary embodiment of a two-piece catheter assembly.

FIG. 13 illustrates an alternate embodiment of a two-piece catheter hub assembly. The catheter hub assembly includes a first catheter hub portion 44 and a second catheter hub portion 46. The first catheter hub portion 44 includes a nose sized to receive a specific needle gage. It is contemplated that the nose of the first catheter hub portion 44 can be sized for various needle gages. The first catheter hub portion 44 also includes an undercut surface 48 to interact with a septum 20 as further described below. The second catheter hub portion 46 includes a free diameter 30 that is necked down via a chamfered surface 31 to a compression diameter 32.

The catheter hub assembly is assembled by first placing a valve 19 into the second catheter hub portion 46. A preformed opening 22 of the septum 20 is disposed in the compression diameter 32 of the second catheter hub portion 46. Subsequently, the first catheter hub portion 44 is inserted into the distal end of the second catheter hub portion 46 and fixed by a weld joint, for example. Accordingly, bellows 24 in the septum 20 allows the septum 20 to contact the undercut surface 48 of the first catheter hub portion 44 and operate in a similar manner as described in the embodiments above. The features of the exemplary catheter hub assembly depicted in FIG. 13 may be combined with features of the other exemplary embodiments disclosed herein.

Figure 14:
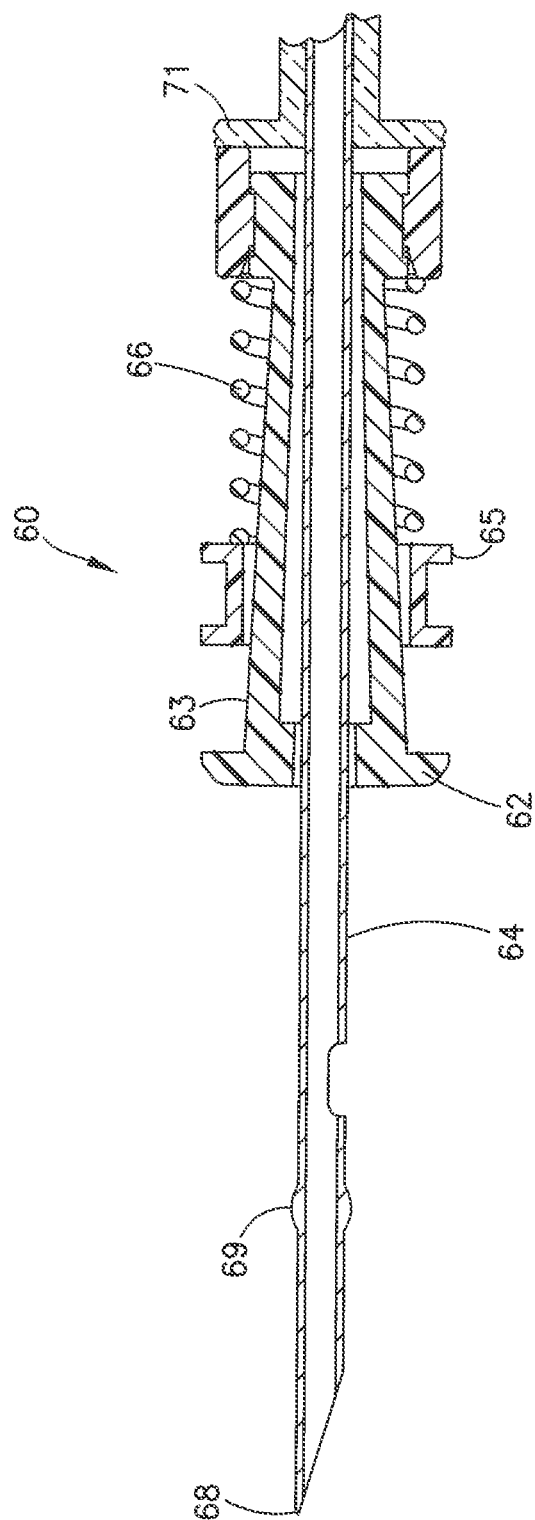
FIG. 14 illustrates a sectional, side view of needle safety mechanism compatible with the catheter hub assembly.

FIG. 14 illustrates an exemplary needle safety mechanism 60 that is compatible with the catheter assembly disclosed in the embodiments herein. The needle safety mechanism 60 includes a needle 64 having a deformation 69 located near a distal tip 68 of the needle 64. The needle 64 is used to enter into a patient's vein. The needle safety mechanism 60 also includes a needle shield 63 having tabs 62 that act as an interlock to engage a catheter hub. A sleeve 65 and spring 66 are disposed in the needle safety mechanism 60 to apply a radial force from the sleeve and axial movement from the spring 66 upon disengagement. The operation of the safety mechanism 60 is described as follows.

The catheter assembly is engaged to the needle safety mechanism 60 while the needle 64 protrudes through the catheter hub as illustrated in FIG. 1. Specifically, the tabs 62 in the needle safety mechanism 60 are engaged to a protrusion in an inner diameter of the catheter hub to prevent the needle safety mechanism 60 from being improperly removed (see FIGS. 17 and 18).

When the catheter tube is placed into the vein of the patient and the user removes the needle from the catheter hub, the tabs 62 in the needle safety mechanism 60 will converge. Upon movement of the tabs 62, the spring 66 releases and applies axial pressure to the sleeve 65 and causes the needle safety mechanism 60 to separate from the catheter hub. As the sleeve 65 moves axially along the needle shield 63, the sleeve 65 applies a radial force to the needle shield 63, causing it to close. Subsequently, the sleeve 65 and the spring 66 extend over the needle shield 63 of the needle safety mechanism 60 and also secure the needle 64 in the needle shield 63 of the needle safety mechanism 60. Accordingly, the needle 64 cannot be accidentally removed from the needle shield 63 of the needle safety mechanism 60 unless the spring 66 is drawn back.

As the user pulls the needle 64 out of the needle safety mechanism 60, the needle deformation 69 will contact an interior end wall 71 of the needle safety mechanism 60. Thus, the user can pull the needle 64 to pull and remove the needle safety mechanism 60 from the catheter hub of the catheter assembly. Also, the needle deformation 69 and the interior end wall 71 prevent the needle 64 from separating from the needle shield 63.

The features of the exemplary needle safety mechanism depicted in FIG. 14 may be combined with features of the other exemplary embodiments disclosed herein. Additionally, a variety of different types of needle safety mechanism can be compatible with the catheter assembly disclosed herein.

Figure 15:
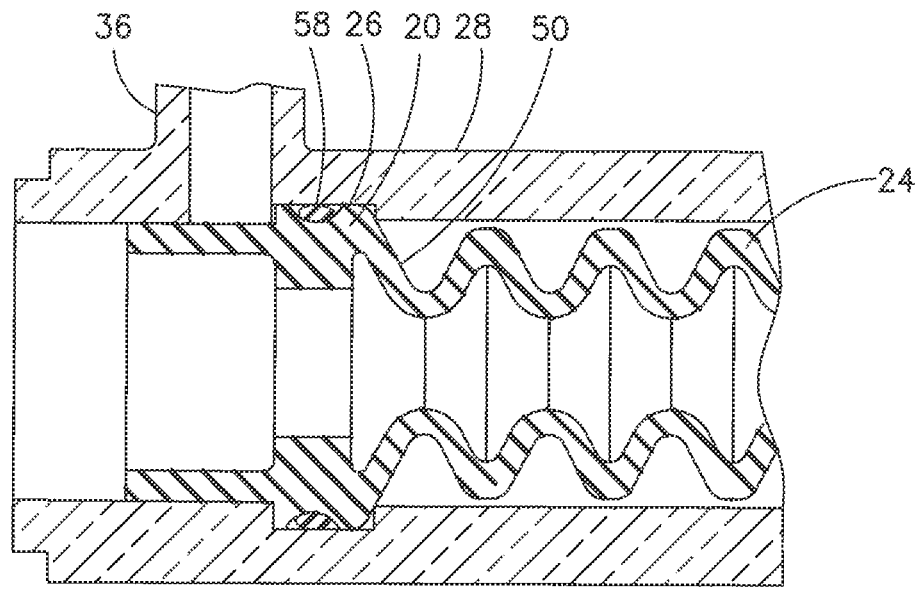
FIG. 15 illustrates a cross sectional view of another exemplary embodiment of a catheter hub assembly including a side port where a septum seals the side port with an O-ring.

FIG. 15 illustrates an exemplary embodiment of an O-ring 58 sealing a catheter hub assembly having a side port 36. Specifically, a septum 50 having a mounting surface 26 is used to seal the side port 36. The operation of the septum 50 with the side port 36 under high fluid pressure is similarly described in the embodiments above.

In the case that high fluid pressure is supplied through the side port 36, the mounting surface 26 flexes and allows fluid to enter the septum 50. The flexing of the mounting surface 26 may unintentionally create a fluid leak path. Thus, the O-ring 58 is disposed adjacent to the side port 36 and between the septum 50 and the catheter hub. The O-ring 58 strengthens the sealing surface between the septum 50 and the catheter hub 28 and ensures that fluid does not flow outside the septum 50 when entering the catheter hub 28. In this manner, the fluid entering from the side port 36 can enter the septum 50 and be appropriately regulated. The features of the exemplary sealing configuration depicted in FIG. 15 may be combined with features of the other exemplary embodiments disclosed herein.

Figure 16:
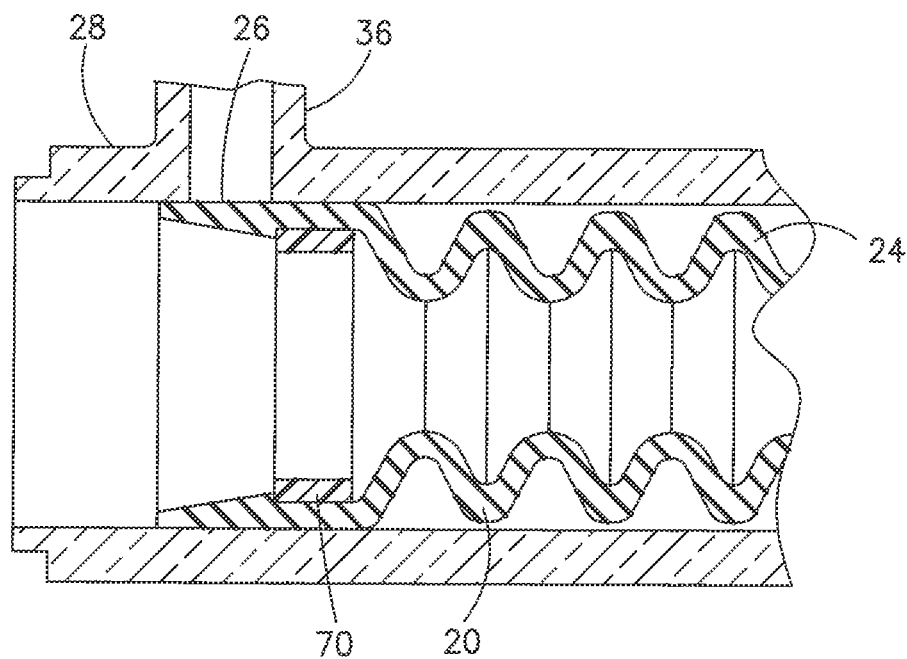
FIG. 16 illustrates a cross sectional view of another exemplary embodiment of a catheter hub assembly including a side port where a septum seals the side port with a compression ring.

FIG. 16 illustrates an exemplary embodiment of a compression ring 70 sealing a catheter hub assembly having a side port 36. Specifically, a septum 20 having a mounting surface 26 is used to seal the side port 36 as similarly described in the above embodiments. The compression ring 70 is used to improve sealing under high fluid pressure from the side port 36 in a similar manner as described in the embodiment of FIG. 15.

The compression ring 70 is disposed adjacent to the side port 36. The compression ring 70 seals the septum 20 to the catheter hub 28 through a press fit, for example, in the septum 20. The press fit causes an increase in pressure between the septum 20 and the catheter hub 28. The increased pressure pinches the septum 20 and reduces the likelihood of a fluid leak path to form where the fluid can flow outside the septum 20 when entering the catheter hub 28. In this manner, the fluid from the side port 36 can enter the septum 20 and be appropriately regulated. The features of the exemplary sealing configuration depicted in FIG. 16 may be combined with features of the other exemplary embodiments disclosed herein.

Figure 17:
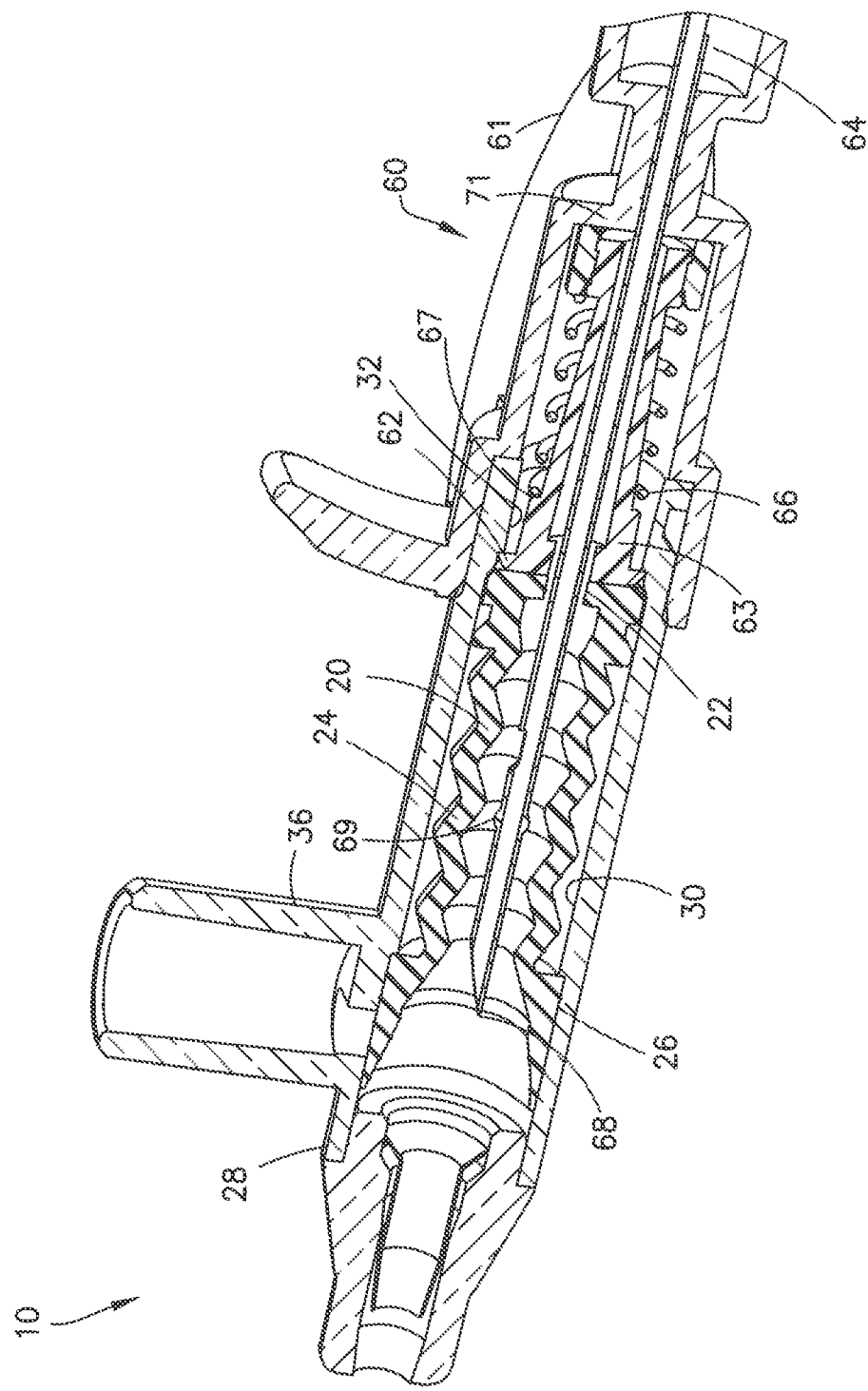
FIG. 17 illustrates a right, side cross sectional view of an exemplary embodiment of a catheter assembly and a needle safety mechanism.
Figure 18:
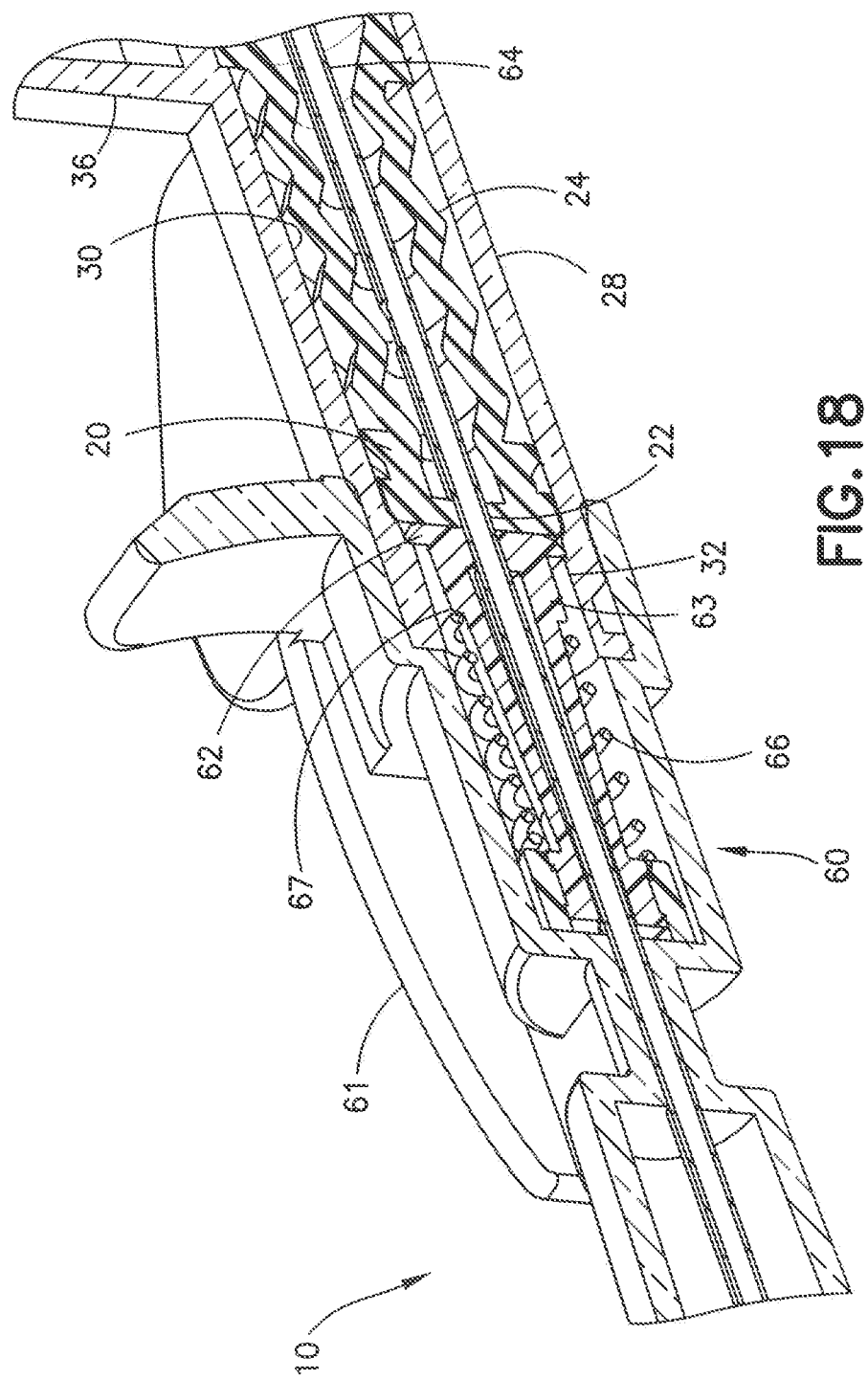
FIG. 18 illustrates a left, side cross sectional view of the exemplary embodiment of FIG. 17 of a catheter assembly and a needle safety mechanism.

FIGS. 17 and 18 illustrate the preferred embodiment of the catheter assembly 10 and the needle safety mechanism 60. This embodiment incorporates the catheter assembly as illustrated in FIGS. 2 and 3-7, as well as a needle safety mechanism 60 similarly illustrated in FIG. 14.

Specifically, when the needle safety mechanism 60 is engaged to the catheter assembly 10, the septum 20 is in the open position. After the catheter tube is set into the vein of the patient, the needle 64 is removed. After the needle 64 is removed from the catheter hub 28 and the distal tip 68 of the needle 64 enters into the needle shield 63, the tabs 62 of the needle shield 63 converge and disengage the catheter hub 28. As the tabs 62 converge, the spring 66 axially extends to close the needle safety mechanism 60, provides a distal barrier to the distal tip 68 of the needle 64 and prevents the distal tip 68 from distal re-exposure.

An outer housing 61 encloses this embodiment of the needle safety mechanism 60. However, the needle safety mechanism 60 does not include the sleeve 65. Instead, the needle shield 63 remains tapered and includes an exterior stepped surface 67. When the tabs 62 of the needle shield 63 disengage the catheter hub 28, the spring 66 is advantageously released from the exterior stepped surface 67 of the tapered needle shield 63. Accordingly, the spring 66 moves axially beyond the exterior stepped surface 67 and continues to surround the exterior of the needle shield 63. The spring 66 ultimately extends to and contacts the tabs 62 of the needle shield 63. Such a configuration radially locks the needle shield 63 into a closed position to prevent the needle 64 from exiting.

When the needle safety mechanism 60 and the catheter hub 28 disengage, the septum 20 moves to the closed position. Specifically, the bellows 24 applies axial pressure and causes the septum 20 to move into the compression diameter 32. The features of the exemplary catheter assembly and the needle safety mechanism depicted in FIGS. 17 and 18 may be combined with features of the other exemplary embodiments disclosed herein.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. A catheter assembly comprising:
a catheter;
a needle having a sharp distal tip; and
a catheter hub connected to the catheter having the needle passing therethrough, the catheter hub including:
a valve having a preformed opening that selectively permits or blocks a flow of fluid through the catheter;
a first inner diameter that closes the valve; and
a second inner diameter larger than the first inner diameter, the second inner diameter opening the valve; wherein
the valve is in a freely open position when the valve is axially compressed into engagement with the second inner diameter of the catheter hub and the preformed opening is unencumbered; and
the valve is in a closed position when the valve is released to engage the first inner diameter of the catheter hub and constrict the preformed opening.

2. The catheter assembly of claim 1, wherein the preformed opening comprises a molded-open slit.

3. The catheter assembly of claim 1, wherein the valve includes a bellows that moves the valve from the open position to the closed position.

4. The catheter assembly of claim 1, wherein the catheter hub further includes a side port.

5. The catheter assembly of claim 4, wherein an angle between a centerline of the side port and a centerline of the catheter hub is less than 90 degrees.

6. The catheter assembly of claim 4, wherein the valve engages the side port to selectively permit or block a flow of fluid through the side port.

7. The catheter assembly of claim 4, wherein the valve selectively permits or blocks a flow of fluid from the catheter and the side port independently.

8. The catheter assembly of claim 1, wherein the valve includes a plurality of axial flow channels.

9. The catheter assembly of claim 1, further comprising a compression ring that compresses the valve to the catheter hub to prevent a flow of fluid from leaking out of the catheter hub.

10. The catheter assembly of claim 1, further comprising an O-ring that seals the valve to the catheter hub to prevent a flow of fluid from leaking out of the catheter hub.

11. The catheter assembly of claim 1, wherein a portion of an inner diameter at a proximal end of the catheter hub does not contact the valve to allow a connector to be centered in the catheter assembly upon engagement with the valve.

12. The catheter assembly of claim 1, wherein:
the needle includes a reduced diameter; and
the reduced diameter of the needle engages the preformed opening of the valve during storage to minimize compression setting of the valve.

13. A catheter assembly comprising:
a catheter;
a needle having a sharp distal tip; and
a catheter hub connected to the catheter having the needle passing therethrough, the catheter hub including:
a valve having a preformed opening that selectively permits or blocks a flow of fluid through the catheter;
a first inner diameter that closes the valve; and
a second inner diameter larger than the first inner diameter, the second inner diameter opening the valve; wherein
the valve is in an open position upon axially compressing the valve into engagement with the second inner diameter of the catheter hub; and
the valve is in a closed position upon releasing the valve to engage the first inner diameter of the catheter hub; and further wherein
the valve includes a bellows that moves the valve from the open position to the closed position and includes a plurality of preformed holes; and
the plurality of preformed holes is disposed between the bellows and the preformed opening.

14. A catheter assembly comprising:
a catheter;
a needle having a sharp distal tip;
a catheter hub connected to the catheter having the needle passing therethrough, the catheter hub including:
a valve having a preformed opening that selectively permits or blocks a flow of fluid through the catheter,
a first inner diameter that closes the valve, and
a second inner diameter larger than the first inner diameter, the second inner diameter opening the valve, and
a needle shield that houses the needle; wherein
the valve is in an open position upon engaging the needle shield to the catheter hub and axially compressing the valve into the second inner diameter of the catheter hub; and
the valve is in a closed position upon disengaging the needle shield from the catheter assembly, thus releasing the valve to engage the first inner diameter of the catheter hub.

15. The catheter assembly of claim 14, wherein:
the needle includes a reduced diameter; and
the reduced diameter of the needle engages the preformed opening of the valve during storage to minimize compression setting of the valve.

16. The catheter assembly of claim 14, wherein the needle shield includes a tab that engages with the catheter hub when the valve is in the open position.

17. The catheter assembly of claim 16, wherein the tab of the needle shield disengages from the catheter hub when the needle is removed.

* * * * *